(12) United States Patent
Hamazaki

(10) Patent No.: US 10,898,058 B2
(45) Date of Patent: Jan. 26, 2021

(54) ENDOSCOPE HAVING COVER AND MOLDED MEMBER EACH FORMING PART OF DISTAL END FACE OF INSERTION SECTION

(71) Applicant: OLYMPUS CORPORATION, Tokyo (JP)

(72) Inventor: Masanori Hamazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 358 days.

(21) Appl. No.: 15/969,820

(22) Filed: May 3, 2018

(65) Prior Publication Data

US 2018/0242822 A1 Aug. 30, 2018

Related U.S. Application Data

(63) Continuation of application No. PCT/JP2016/079328, filed on Oct. 3, 2016.

(30) Foreign Application Priority Data

Nov. 9, 2015 (JP) ................................. 2015-219527

(51) Int. Cl.
*A61B 1/00* (2006.01)
*A61B 1/05* (2006.01)
(Continued)

(52) U.S. Cl.
CPC ........ *A61B 1/00096* (2013.01); *A61B 1/0008* (2013.01); *A61B 1/0011* (2013.01);
(Continued)

(58) Field of Classification Search
None
See application file for complete search history.

(56) References Cited

U.S. PATENT DOCUMENTS 4,856,495 A * 8/1989 Tohjoh ............... A61B 1/00096
600/175
4,971,035 A * 11/1990 Ito ......................... A61B 1/018
348/65

(Continued)

FOREIGN PATENT DOCUMENTS

JP S56-130135 A 10/1981
JP S56-133802 A 10/1981
(Continued)

OTHER PUBLICATIONS

Machine Translateion of JP 2003210388(A) Hamazaki Masanori Jul. 29, 2003.*

(Continued)

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope includes a distal end rigid member, a distal end member, an optical unit, an opening provided in the distal end member, and a ring-shaped molded member configured to engage with a ring-shaped space formed between an outer circumferential surface in the distal end portion in an axial direction of the optical member and an inner circumferential surface in the opening of the distal end member, inclined from the distal end face of the distal end member toward the distal end face on an outer circumferential surface of the optical member throughout a whole circumference.

6 Claims, 6 Drawing Sheets

(51) Int. Cl.
*A61B 1/12* (2006.01)
*G02B 23/24* (2006.01)

(52) U.S. Cl.
CPC ...... *A61B 1/00078* (2013.01); *A61B 1/00163* (2013.01); *A61B 1/051* (2013.01); *A61B 1/12* (2013.01); *G02B 23/243* (2013.01); *G02B 23/2423* (2013.01)

(56) References Cited

U.S. PATENT DOCUMENTS

| | | | | |
|---|---|---|---|---|
| 5,711,756 | A * | 1/1998 | Chikama | A61B 1/00096 600/112 |
| 6,790,175 | B1 * | 9/2004 | Furusawa | A61B 5/0066 600/128 |
| 8,314,835 | B2 * | 11/2012 | Kanzaki | A61B 1/00059 348/362 |
| 2006/0009681 | A1 * | 1/2006 | Tanaka | A61B 8/4488 600/160 |
| 2006/0264919 | A1 * | 11/2006 | Schaaf | A61B 1/00165 606/15 |
| 2007/0118020 | A1 * | 5/2007 | Miyagi | A61B 1/00091 600/177 |
| 2007/0173695 | A1 * | 7/2007 | Hirata | A61B 1/0615 600/152 |
| 2007/0260113 | A1 * | 11/2007 | Otawara | A61B 1/043 600/104 |
| 2008/0114205 | A1 * | 5/2008 | Kagawa | A61B 1/00071 600/139 |
| 2008/0132760 | A1 * | 6/2008 | Takeuchi | A61B 1/00165 600/129 |
| 2008/0167529 | A1 * | 7/2008 | Otawara | A61B 1/07 600/168 |
| 2009/0156898 | A1 * | 6/2009 | Ichimura | A61B 1/00096 600/127 |
| 2009/0244727 | A1 * | 10/2009 | Ishii | G02B 23/2476 359/819 |
| 2010/0152540 | A1 * | 6/2010 | Tanoue | G02B 23/2469 600/175 |
| 2011/0112363 | A1 | 5/2011 | Koga et al. | |
| 2014/0058201 | A1 * | 2/2014 | Mizuyoshi | A61B 1/0011 600/129 |
| 2014/0275786 | A1 | 9/2014 | Goto et al. | |

FOREIGN PATENT DOCUMENTS

| | | |
|---|---|---|
| JP | 2003-210388 A | 7/2003 |
| JP | 3845311 B2 | 11/2006 |
| JP | 2011-120863 A | 6/2011 |

OTHER PUBLICATIONS

International Search Report dated Dec. 13, 2016 issued in PCT/JP2016/079328.

Extended Supplementary European Search Report dated May 31, 2019 in European Patent Application No. 16 86 3920.1.

* cited by examiner

ENDOSCOPE HAVING COVER AND MOLDED MEMBER EACH FORMING PART OF DISTAL END FACE OF INSERTION SECTION

CROSS REFERENCE TO RELATED APPLICATION

This application is a continuation application of PCT/JP2016/079328 filed on Oct. 3, 2016 and claims benefit of Japanese Application No. 2015-219527 filed in Japan on Nov. 9, 2015, the entire contents of which are incorporated herein by this reference.

BACKGROUND OF THE INVENTION

Field of the Invention

The present invention relates to an endoscope provided with a distal end member configured to constitute a distal end face of an insertion portion to be inserted into a subject and a columnar member disposed in the distal end member and configured to constitute a distal end face at a position different from the distal end face formed by the distal end member in an axial direction of the insertion portion.

Description of the Related Art

Today, endoscopes inserted into a subject are widely used in medical and industrial fields. The endoscopes can observe an interior of the subject by inserting an elongated insertion portion into the subject.

Part of an outer circumferential surface and a distal end face of a distal end rigid member configured to constitute a distal end portion provided on a distal end side of the insertion portion of the endoscope is covered with a distal end cover which is the distal end member. An image pickup unit which is a columnar member and which picks up an image of an interior of the subject is provided inside the distal end rigid member inside the distal end cover.

In the image pickup unit, an objective lens which is positioned on a topmost side among a plurality of lenses in an optical unit configured to constitute the image pickup unit protrudes from a distal end of the distal end cover configured to constitute a distal end face of the insertion portion in the case of, for example, a front-view type endoscope. A lens surface of the objective lens together with the distal end of the distal end cover is provided so as to configure the distal end face of the insertion portion.

Note that an illumination window configured to supply illumination light to the interior of the subject and a distal end opening of a suction pipe that also serves as a known treatment instrument insertion pipe are provided in addition to the objective lens at the distal end of the distal end cover. In addition, a distal end opening of a front water feeding pipe configured to supply a liquid into the subject and a nozzle of a fluid supply pipe configured to supply a fluid to the lens surface of the objective lens (hereinafter referred to as "fluid supply nozzle") or the like are provided. These parts constitute the distal end face of the insertion portion respectively.

Furthermore, Japanese Patent No. 3845311 discloses a configuration in which a lens surface of an objective lens is positioned so as to protrude more forward than a distal end of a distal end cover and a circumferential slope inclined toward the lens surface is provided at the distal end of the distal end cover positioned around an outer circumference on the lens surface of the objective lens. As a result, when a fluid is supplied from a fluid supply nozzle to the lens surface of the objective lens, the circumferential slope of the distal end cover improves water removing performance from the lens surface and cleaning/disinfecting performance of the lens surface.

Note that a configuration is also known in which the lens surface of the objective lens is positioned recessed more backward than the distal end of the distal end cover and a circumferential slope inclined toward the lens surface is provided at the distal end of the distal end cover positioned around an outer circumference of the lens surface of the objective lens. As a result, when the fluid is supplied to the lens surface of the objective lens from the fluid supply nozzle, the circumferential slope of the distal end cover improves water removing performance from the lens surface and cleaning/disinfecting performance of the lens surface.

Here, in the endoscope disclosed in Japanese Patent No. 3845311, part of the outer circumferential surface of the objective lens is bonded to an inner circumferential surface of the objective lens insertion hole formed at the distal end of the distal end cover via an adhesive.

Note that a gap between the inner circumferential surface of an objective lens insertion hole and part of the outer circumferential surface of the objective lens is filled with the adhesive such that the distal end becomes a circumferential slope continuous and gentle to the circumferential slope provided at the distal end of the distal end cover and having a similar angle of inclination. That is, the adhesive also configures the distal end face of the insertion portion.

SUMMARY OF THE INVENTION

An endoscope according to one aspect of the present invention includes a distal end rigid member disposed at a distal end of an insertion portion to be inserted into a subject, a distal end member configured to constitute part of a distal end face of the insertion portion by covering a surface on at least a distal end side of the distal end rigid member, an optical unit including an optical member and a frame member configured to hold an outer circumferential surface of a distal end portion of the optical member while leaving the outer circumferential surface of the distal end portion of the optical member exposed, disposed in the distal end rigid member and configured to constitute part of the distal end face of the insertion portion with an objective surface of the optical member at a position different from the distal end face formed by the distal end member in an axial direction of the insertion portion, an opening provided in the distal end member, configured to expose the distal end portion of the optical member to the distal end side of the insertion portion with the optical unit being attached to the distal end rigid member and having an inner diameter larger than an outside diameter of the distal end portion in the axial direction of the optical member, and a ring-shaped molded member configured to engage with a ring-shaped space formed between the outer circumferential surface in the distal end portion in an axial direction of the optical member and an inner circumferential surface in the opening of the distal end member and inclined from the distal end face of the distal end member toward the distal end face on an outer circumferential surface of the optical member throughout a whole circumference.

DETAILED DESCRIPTION OF THE PREFERRED EMBODIMENT(S)

Hereinafter, embodiments of the present invention will be described with reference to the accompanying drawings. Note that the drawings are schematic ones and a thickness-width relationship of each member and a thickness ratio among respective members or the like are different from the real ones, and it goes without saying that parts differing in a dimensional relationship or ratio among drawings are included.

First Embodiment

Figure 1:
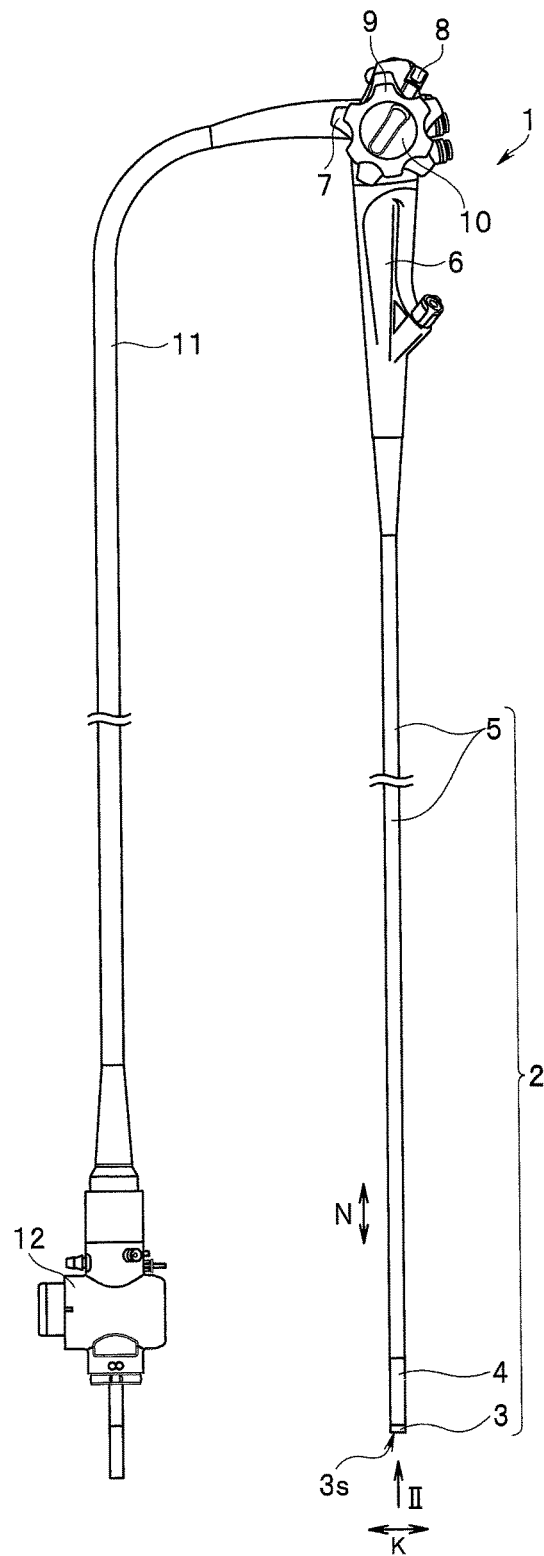
FIG. 1 is a diagram illustrating an endoscope according to a first embodiment.

FIG. 1 is a diagram illustrating an endoscope according to the present embodiment. As shown in FIG. 1, the endoscope 1 is mainly constructed of an insertion portion 2 inserted into a subject, an operation portion 6 connected to a proximal end side of the insertion portion 2, a universal cord 11 extending from the operation portion 6 and a connector 12 provided at an extending end of the universal cord 11. Note that the endoscope 1 is electrically connected to an external apparatus such as a control apparatus or an illumination apparatus via the connector 12.

The operation portion 6 is provided with a vertical bending operation knob 7 configured to cause the bending portion 4 of the insertion portion 2 to bend in a vertical direction and a lateral bending operation knob 9 configured to cause the bending portion 4 to bend in a lateral direction.

Furthermore, the operation portion 6 is provided with a fixing lever 8 configured to fix a rotation position of the vertical bending operation knob 7 and a fixing knob 10 configured to fix a rotation position of the lateral bending operation knob 9.

The insertion portion 2 is constructed of a distal end portion 3, the bending portion 4 and a flexible pipe portion 5 in order from the distal end side and formed into an elongated shape along a longitudinal axial direction N.

The bending portion 4 is bent in, for example, four directions of up, down, left and right through rotation operations of the vertical bending operation knob 7 and the lateral bending operation knob 9. In this way, the bending portion 4 is intended to vary an observation direction of an image pickup unit 50 (see FIG. 3) provided in the distal end portion 3 or improve insertion performance of the distal end portion 3 in the subject. Furthermore, the flexible pipe portion 5 is connected to a proximal end side of the bending portion 4.

Next, a configuration of a distal end face 3s of the distal end portion 3 and a configuration of an interior of the distal end portion 3 will be described using FIG. 2 to FIG. 4.

Figure 2:
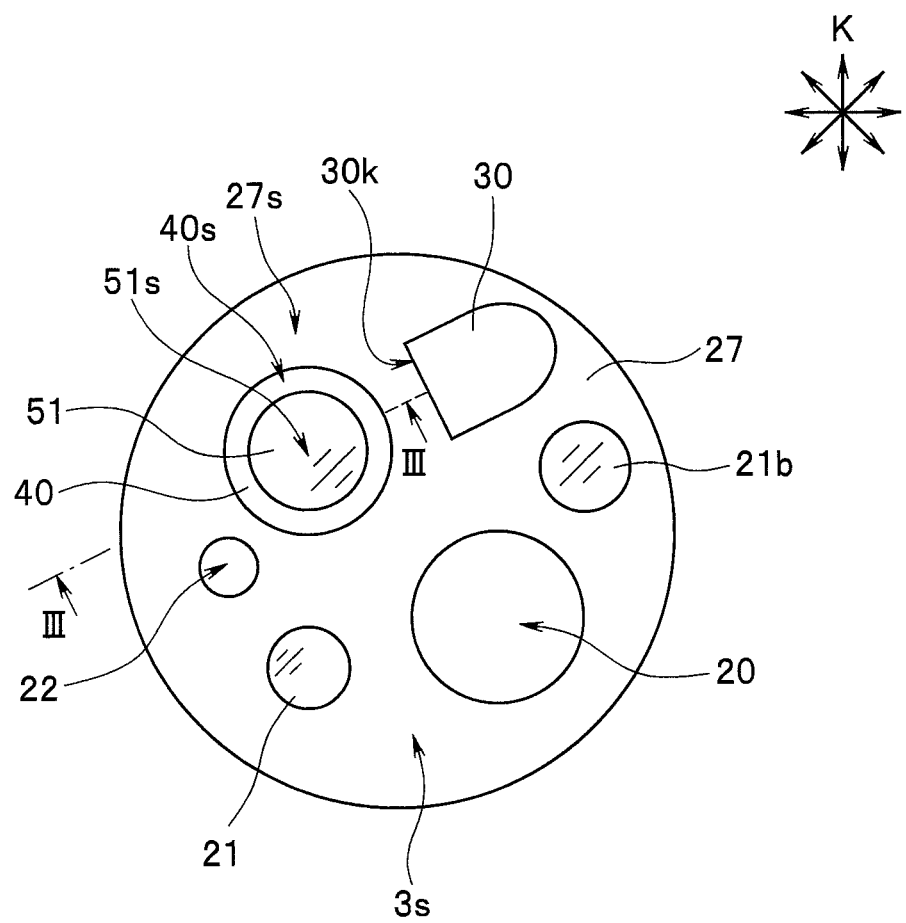
FIG. 2 is a plan view of a distal end face at a distal end portion of an insertion portion seen from a direction II in FIG. 1.
Figure 3:
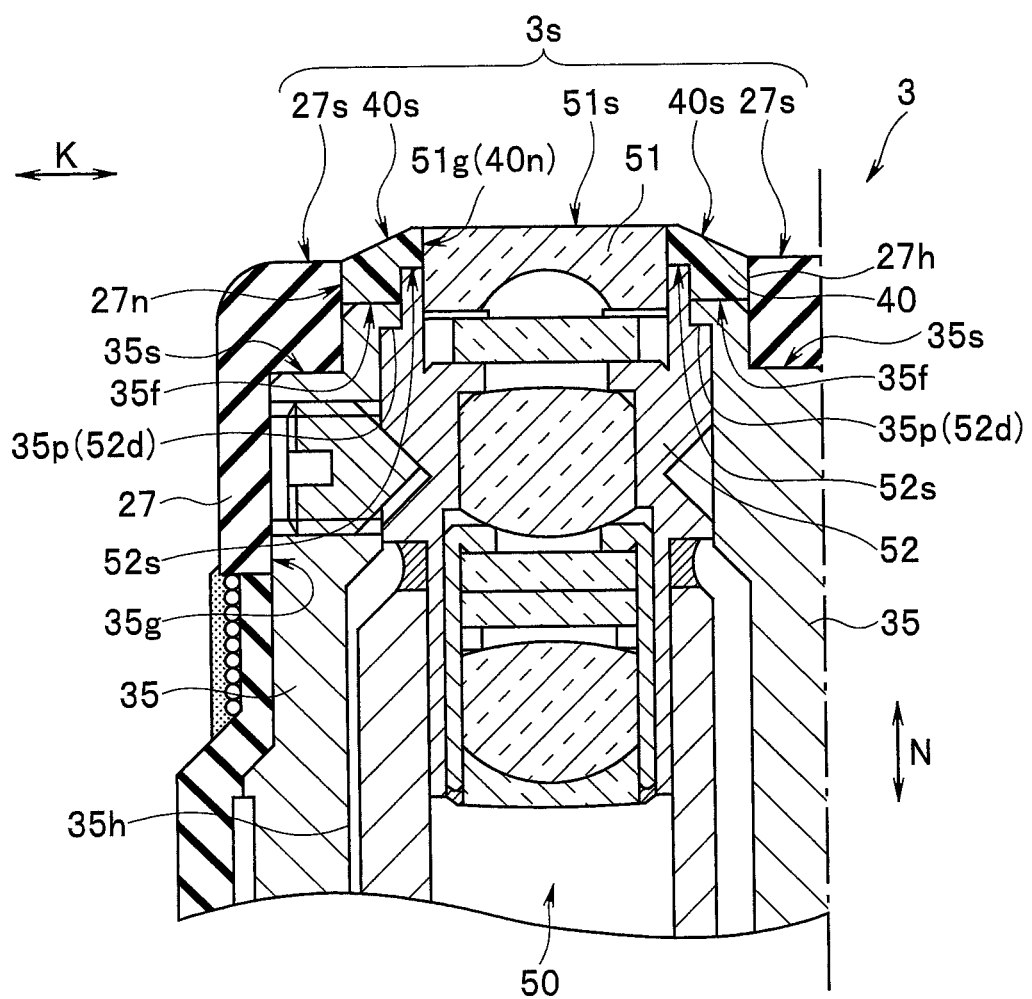
FIG. 3 is a partial cross-sectional view of the distal end portion along a line in FIG. 2.
Figure 4:
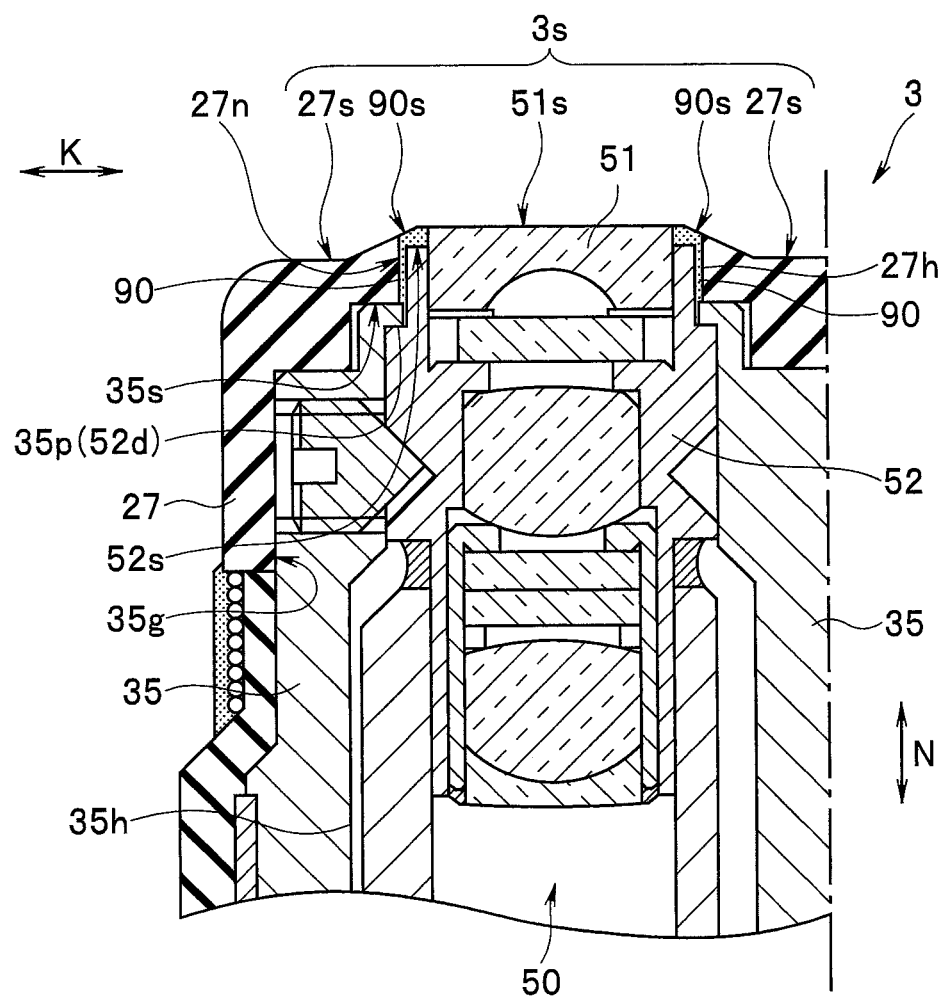
FIG. 4 is a partial cross-sectional view of a conventional distal end portion.

FIG. 2 is a plan view of a distal end face of the distal end portion of the insertion portion seen from a direction II in FIG. 1, FIG. 3 is a partial cross-sectional view of the distal end portion along a line in FIG. 2 and FIG. 4 is a partial cross-sectional view of a conventional distal end portion.

As shown in FIG. 2 and FIG. 3, part of an outer circumferential surface 35g and a distal end face 35s on the distal end side of a distal end rigid member 35 configured of, for example, metal that configures the distal end portion 3 is covered with a distal end cover 27 which is a distal end member made of, for example, polysulfone. Note that the distal end rigid member 35 may also be made of anything other than metal, for example, resin.

A distal end 27s of the distal end cover 27, that is, a region of the distal end rigid member 35 that covers a distal end face 35s constitutes part of a distal end face 3s of the distal end portion 3. The member that constitutes the distal end cover 27 is not limited to polysulfone, but may be any biocompatible, chemical-resistant and nonconductive member.

An image pickup unit arrangement hole 35h along a longitudinal axial direction N of the insertion portion 2 is formed in the distal end rigid member 35. An image pickup unit 50 configured to observe an interior of the subject, the image pickup unit 50 being a columnar member and constructed of a plurality of lenses, an image pickup device and a frame member that holds the lenses and the image pickup device, or the like is provided in the image pickup unit arrangement hole 35h. That is, the image pickup unit 50 is provided inside the distal end cover 27.

The image pickup unit 50 is positioned in the longitudinal axial direction N with respect to the image pickup unit arrangement hole 35h with a stepped portion 52d provided on a distal end side of an outer circumferential surface of the lens frame 52 configured to constitute the image pickup unit 50 abutting against an abutting surface 35p formed on a distal end side of the inner circumferential surface facing the image pickup unit arrangement hole 35h of the distal end rigid member 35.

More specifically, the image pickup unit 50 is positioned in the longitudinal axial direction N with respect to the image pickup unit arrangement hole 35h such that a lens surface 51s of the objective lens 51 which is the distal end of the image pickup unit 50 is positioned so as to protrude more forward than the distal end 27s.

Note that although not shown, the image pickup unit 50 may also be positioned in the longitudinal axial direction N with respect to the image pickup unit arrangement hole 35h such that the lens surface 51s of the objective lens 51 which is the distal end of the image pickup unit 50 is positioned so as to be recessed more backward than the distal end 27s.

In addition to the aforementioned objective lens 51, an illumination window 21 configured to supply illumination light into the subject and an opening 22 of a front water feeding pipe configured to supply a liquid into the subject are provided in a region of the distal end face 35s of the distal end rigid member 35 not covered with the distal end cover 27. Furthermore, a distal end opening 20 of a suction pipe also configured to serve as a known treatment instrument insertion pipe, a fluid supply nozzle 30 configured to supply a fluid from a supply port 30k toward the lens surface 51s of the objective lens 51 and a distal end 40s of a molded member 40 or the like are provided.

In other words, the distal end cover 27 covers a region of the distal end face 35s except the objective lens 51, the illumination window 21, the opening 22, the distal end opening 20, the fluid supply nozzle 30 and the molded member 40. Note that the members also constitute the distal end face 3s.

The molded member 40 is positioned between the distal end cover 27 and the image pickup unit 50 in a diameter direction K of the insertion portion 2 as shown in FIG. 2 and FIG. 3.

More specifically, the molded member 40 is bonded and fixed to the distal end face 35s and a distal end face 35f, a distal end face 52s of the lens frame 52, part of an outer circumferential surface 51g of the objective lens 51 and an inner circumferential surface 27n of the distal end cover 27.

Note that the inner circumferential surface 27n is a surface formed in the distal end 27s along the longitudinal axial direction N and facing the molded member 40 inside an insertion hole 27h communicating with an image pickup unit arrangement hole 50h in the diameter direction K.

The molded member 40 is positioned with an inside surface 40n in the diameter direction K abutting against part of the outer circumferential surface 51g of the objective lens 51. This is intended to reduce the amount of adhesive used for bonding the surface 40n and part of the outer circumferential surface 51g.

The molded member 40 is molded of resin in advance, and as shown in FIG. 2, is ring-shaped so as to surround the objective lens 51 around an outer circumference of the objective lens 51. The molded member 40 is formed such that the distal end 40s is gently inclined from the distal end 27s toward the lens surface 51s. Note that the distal end 40s constitutes the distal end face 3s.

Note that although the distal end 40s is formed into a shape inclined forward, in the case where the lens surface 51s is positioned recessed more backward than the distal end 27s, the distal end 40s may be formed into a shape inclined backward.

The molded member 40 is preferably made of resin since resin has impact resistance and excellent workability. However, the molded member 40 may also be formed of another material such as ceramics as long as the molded member 40 exhibits impact resistance, chemical resistance, biocompatibility and non-conductivity since the molded member 40 is in contact with the image pickup unit 50.

Note that since the rest of the configuration inside the distal end portion 3 and the configuration of the distal end face 3s are well known, description of the configurations is omitted.

Next, a method for assembling the distal end portion 3 according to the present embodiment will be described briefly. First, an operator inserts the image pickup unit 50 into the image pickup unit arrangement hole 35h of the distal end rigid member 35 from behind until the stepped portion 52d abuts against the abutting surface 35p and fixes the image pickup unit 50. As a result, the distal end side of the image pickup unit 50 penetrates the insertion hole 27h.

After that, the operator puts the molded member 40 over the distal end face 35s and the distal end face 52s from more forward than the distal end face 35f so as to come into contact with the distal end face 35s and the distal end face 52s, and bonds and fixes the molded member 40 to the distal end face 35f, the distal end face 52s and part of the outer circumferential surface 51g.

Finally, the operator puts the distal end cover 27 over the distal end rigid member 35 from more forward than the distal end face 35s such that the objective lens 51, the illumination window 21, the opening 22, the distal end opening 20, the fluid supply nozzle 30 and the molded member 40 are exposed, and bonds and fixes the distal end cover 27 to the molded member 40 and the distal end rigid member 35.

Note that since the rest of the assembly method is well known, description of the assembly method is omitted.

Thus, the present embodiment has described that the distal end face 3s includes a ring-shaped molded member 40 configured to circumferentially surround the objective lens 51 between the distal end cover 27 and the image pickup unit 50 in the diameter direction K of the insertion portion 2. Furthermore, the present embodiment also has described that the distal end 40s of the molded member 40 is formed into a shape gently inclined from the distal end 27s toward the lens surface 51s.

In a conventional configuration of the distal end face 3s, as shown in FIG. 4, part of the outer circumferential surface 51g of the objective lens 51 is bonded to the inner circumferential surface 27n facing the insertion hole 27h formed with a large diameter in consideration of an assembly error on the distal end sides of the image pickup unit 50 in the distal end cover 27 via an adhesive 90 with which the insertion hole 27h is filled. A distal end 90s of the adhesive 90 also fills the gap between the inner circumferential surface 27n of the insertion hole 27h and part of the outer circumferential surface 51g of the objective lens 51 so as to become a circumferential slope continuous and gentle to the circumferential slope provided at the distal end 27s and having a similar angle of inclination, and the adhesive 90 also constitutes the distal end face 3s.

However, in such a conventional configuration, since the distal end 90s of the adhesive 90 exposed in the distal end face 3s has a large area as shown in FIG. 4, when exposed to body fluids such as a gastric acid or a cleaning/disinfecting liquid or the like for an extended period of time as described above, the adhesive 90 deteriorates with time. Furthermore, projections and recesses are formed on the distal end 90s and the liquid stagnates at the projections and recesses causing a problem that draining performance of the lens surface 51s declines.

In contrast, in the configuration of the present embodiment, the molded member 40 formed of, for example, resin as a member separate from the distal end cover 27 is used instead of the conventional adhesive 90. This prevents the distal end 40s formed on the slope of the molded member 40 from deteriorating with time due to long-term use and allows smoothness of the slope to be maintained.

This allows the fluid jetted out of the supply port 30k to smoothly arrive at the lens surface 51s without stagnating at the distal end 40s and flow out of the lens surface 51s, thus preventing deterioration of draining performance of the lens surface 51s. This also prevents the objective lens 51 from falling off.

Note that although the present embodiment also uses an adhesive to fix the molded member 40, the area of the adhesive exposed to the liquid on the distal end face 3s is smaller in the configuration of the present embodiment than the conventional configuration shown in FIG. 4, and so deterioration with time of the adhesive can be ignored. That is, the distal end face 3s has a configuration with excellent chemical resistance.

Furthermore, the conventional configuration in FIG. 4 requires high accuracy workability of the insertion hole 27h with respect to the distal end cover 27 and high accuracy assembly performance on the distal end side of the image pickup unit 50 with respect to the insertion hole 27h in order to reduce the exposed area of the adhesive 90. However, the present embodiment does not require high accuracy workability or assembly performance, and the present embodiment can be implemented with workability or assembly performance of the distal end cover 27 equivalent to the conventional workability or assembly performance.

As described above, it is possible to provide the endoscope 1 provided with the configuration capable of improving durability of the slope of the distal end face 3s of the insertion portion 2 and water removing performance using the slope while securing workability and assembly performance of the distal end cover 27.

Second Embodiment

Figure 5:
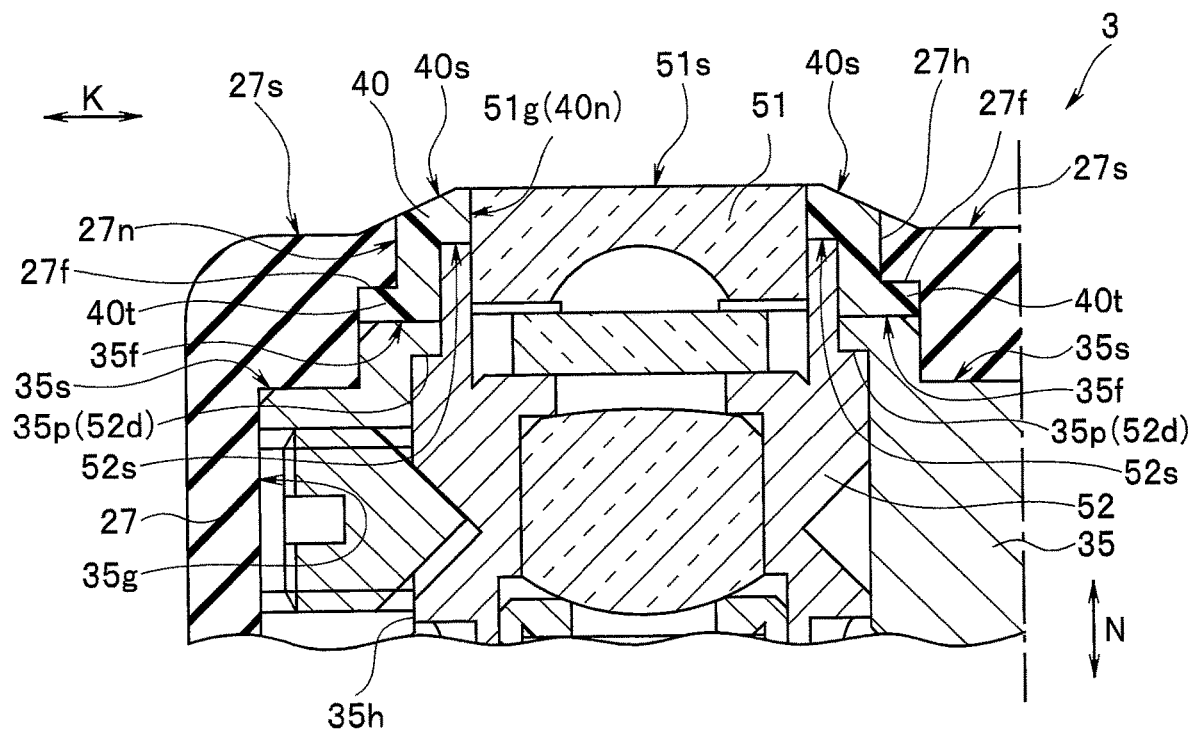
FIG. 5 is a partial cross-sectional view of a distal end portion of an endoscope according to a second embodiment.

FIG. 5 is a partial cross-sectional view of a distal end portion of an endoscope of the present embodiment.

The configuration of the endoscope according to the second embodiment is different from the aforementioned endoscope of the first embodiment shown in FIG. 1 to FIG. 3 in that the molded member is provided with a slip prevention abutting portion and a surface with which the abutting portion is in contact is formed on the inner circumferential surface facing the insertion hole of the distal end cover 27.

Thus, only the differences will be described and the same components as the components of the first embodiment are assigned the same reference numerals and description of the components is omitted.

As shown in FIG. 5, in the distal end portion 3 of the endoscope 1 of the present embodiment, the molded member 40 is formed into a shape having an abutting portion 40t abutting against a surface 27f along the diameter direction K in the inner circumferential surface 27n facing the insertion hole 27h of the distal end cover 27 on the proximal end side.

Note that the rest of the configuration and assembly method are the same as the configuration and assembly method of the aforementioned first embodiment.

According to such a configuration, the abutting portion 40t of the molded member 40 abuts against the surface 27f along the diameter direction K of the inner circumferential surface 27n of the distal end cover, and the distal end cover 27 thereby functions as a stopper preventing the molded member 40 from slipping off forward. Thus, such a configuration can prevent the molded member 40 from slipping off more reliably than the first embodiment, and so the molded member 40 has higher durability compared to the first embodiment.

As a result, the possibility that projections and recesses will be formed on the distal end face 3s becomes lower compared to the first embodiment, and it is possible to more reliably secure water removing performance using the slope of the distal end face 3s. Note that the other effects are the same as the effects of the aforementioned first embodiment.

Third Embodiment

Figure 6:
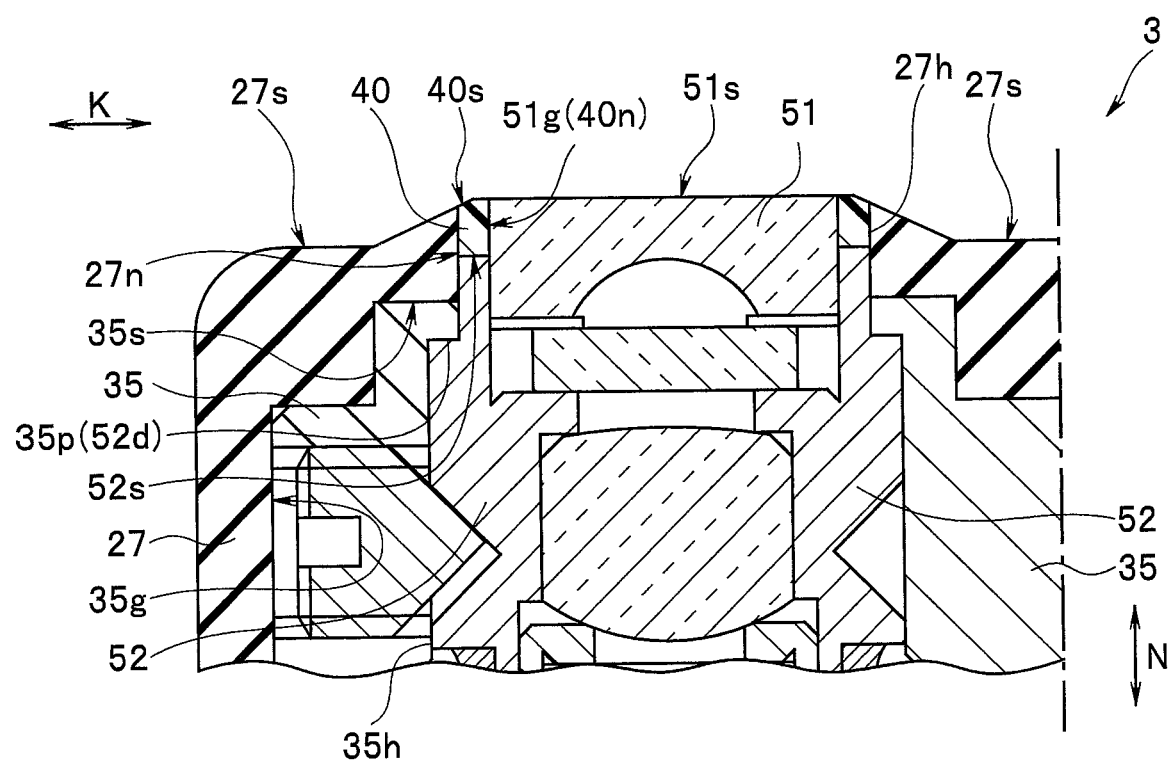
FIG. 6 is a partial cross-sectional view of a distal end portion of an endoscope according to a third embodiment.

FIG. 6 is a partial cross-sectional view of a distal end portion of an endoscope according to the present embodiment.

The configuration of the endoscope according to the third embodiment is different from the aforementioned endoscope according to the first embodiment shown in FIG. 1 to FIG. 3 and the endoscope according to the second embodiment shown in FIG. 4 in that the outside diameter of the molded member is substantially equal to the outside diameter on the distal end side of the image pickup unit.

Thus, only the differences will be described and the same components as the components of the first and second embodiments are assigned the same reference numerals and description of the components is omitted.

As shown in FIG. 6, in the distal end portion 3 of the endoscope 1 according to the present embodiment, the molded member 40 has an outside diameter substantially the same as the outside diameter on the distal end side of the lens frame 52, and the distal end face 52s of the lens frame 52, part of the outer circumferential surface 51g are bonded and fixed to the inner circumferential surface 27n and not bonded or fixed to the distal end face 35s.

Note that the rest of the configuration is the same as the configuration of the endoscope 1 of the aforementioned first and second embodiments.

Next, a method for assembling the distal end portion 3 according to the present embodiment will be described briefly. First, the operator inserts the image pickup unit 50 in which the molded member 40 is bonded and fixed to the distal end face 52s of the lens frame 52 into the image pickup unit arrangement hole 35h of the distal end rigid member 35 from behind until the stepped portion 52d abuts against the abutting surface 35p and fixes the image pickup unit 50. As a result, the distal end side of the image pickup unit 50 penetrates the insertion hole 27h.

Finally, the operator puts the distal end cover 27 over the distal end rigid member 35 from more forward than the distal end face 35s such that the objective lens 51, the illumination window 21, the opening 22, the distal end opening 20, the fluid supply nozzle 30 and the molded member 40 are exposed. Note that since the rest of the assembly method is well known, description of the assembly method is omitted.

According to such a configuration, in the first and second embodiments, the image pickup unit 50 needs to be assembled to the distal end rigid member 35 and the molded member 40 then needs to be assembled.

However, in the configuration of the present embodiment, since the molded member 40 can be assembled to the distal end rigid member 35 together with the image pickup unit 50, the assembly performance of the distal end portion 3 improves. Note that other effects are the same as the effects of the aforementioned first and second embodiments.

Note that modifications will be described below. In the aforementioned first to third embodiments, it has been described that the lens surface 51s of the objective lens 51 protrudes more forward than the distal end 27s of the distal end cover 27 and a circumferential slope by the distal end 40s of the molded member 40 is formed on the distal end face 3s.

Regardless of such a configuration, even when the distal end 40s has no slope, that is, the distal end face 3s is formed into a flat surface, although water draining performance of the lens surface 51s may decline, effects similar to the effects of the aforementioned first to third embodiments can be obtained. In other words, the modification is also applicable to the configuration of the endoscope in which the distal end face 3s is formed to be flat.

Furthermore, in the aforementioned first to third embodiments, the columnar member is described as the image pickup unit 50, but regardless of this, the columnar member may be a simple lens unit constructed of only an optical system or may be a unit in which a single lens unit is held by a lens frame.

Furthermore, in the aforementioned first to third embodiments, the distal end member is described as the distal end cover 27, but regardless of this, it goes without saying that the distal end member may be the distal end rigid member 35.

What is claimed is:

1. An endoscope comprising:

a distal end rigid member disposed at a distal end of an insertion portion to be inserted into a subject;

a distal end cover forming a first part of a distal end face of the insertion portion, the distal end cover covering a surface on at least a distal end side of the distal end rigid member;

an optical unit comprising an optical member and a frame, the frame being configured to hold an outer circumferential surface of the optical member except a distal end portion of the outer circumferential surface to expose the distal end portion of the outer circumferential surface, the optical unit being disposed in the distal end rigid member such that an objective surface of the optical member forms a second part of the distal end face of the insertion portion at a position different from the first part of the distal end face formed by the distal end cover in an axial direction of the insertion portion;

an opening provided in the distal end cover, the opening being configured to expose the distal end portion of the optical member to the distal end side of the insertion portion with the optical unit being attached to the distal end rigid member, the opening having an inner diameter larger than an outside diameter of the distal end portion in the axial direction of the optical member;

a ring-shaped molded member disposed in a ring-shaped space formed between the outer circumferential surface in the distal end portion in an axial direction of the optical member and an inner circumferential surface in the opening of the distal end cover, the molded member having a surface inclined from the distal end face of the distal end cover toward the distal end face on an outer circumferential surface of the optical member throughout a whole circumference of the outer circumferential surface of the optical member; and an adhesive filled between the outer circumferential surface and the molded member and between the inner circumferential surface and the molded member, the adhesive being configured to fix the molded member to the outer circumferential surface and to the inner circumferential surface.

2. The endoscope according to claim 1, wherein the molded member is made of resin.

3. The endoscope according to claim 1, wherein the molded member comprises an abutting portion configured to abut against a surface of the distal end cover along the diameter direction positioned closer to a proximal end side in the axial direction than to the distal end face formed on the distal end cover.

4. The endoscope according to claim 1, wherein the optical unit comprises an image pickup unit configured to observe an interior of the subject, and an objective lens positioned on the distal end side of the image pickup unit forms the objective surface of the optical member.

5. The endoscope according to claim 1, wherein a surface inside the molded member in the diameter direction abuts against the outer circumferential surface in the distal end portion in the axial direction of the optical member.

6. The endoscope according to claim 1, wherein the objective surface of the optical member is positioned distally relative to the distal end face formed by the distal end cover.

* * * * *